United States Patent
McGuckin, Jr. et al.

(10) Patent No.: US 7,179,275 B2
(45) Date of Patent: Feb. 20, 2007

(54) VEIN FILTER

(75) Inventors: James F. McGuckin, Jr., Radnor, PA (US); Richard T. Briganti, Malvern, PA (US); Stephan A. DeFonzo, Wayne, PA (US); John H. Thinnes, Jr., Philadelphia, PA (US)

(73) Assignee: Rex Medical, L.P., Conshohocken, PA (US)

( * ) Notice: Subject to any disclaimer, the term of this patent is extended or adjusted under 35 U.S.C. 154(b) by 209 days.

(21) Appl. No.: 10/697,211

(22) Filed: Oct. 30, 2003

(65) Prior Publication Data

US 2005/0004596 A1  Jan. 6, 2005

Related U.S. Application Data

(63) Continuation-in-part of application No. 10/638,846, filed on Aug. 11, 2003, which is a continuation of application No. 09/883,819, filed on Jun. 18, 2001, now Pat. No. 6,623,506.

(60) Provisional application No. 60/466,807, filed on Apr. 30, 2003.

(51) Int. Cl.
*A61M 29/00* (2006.01)

(52) U.S. Cl. .................................................. 606/200

(58) Field of Classification Search ................ 606/200, 606/191, 194, 110, 113, 114, 127
See application file for complete search history.

(56) References Cited

U.S. PATENT DOCUMENTS 3,952,747 A    4/1976  Kimmel, Jr.
4,425,908 A    1/1984  Simon
4,494,531 A    1/1985  Gianturco
4,512,338 A    4/1985  Balko et al.
4,619,246 A   10/1986  Molgaard-Nielsen et al.
4,688,553 A    8/1987  Metals
4,727,873 A    3/1988  Mobin-Uddin (Continued)

FOREIGN PATENT DOCUMENTS

WO    WO 9312723    7/1993

(Continued)

OTHER PUBLICATIONS

B. Braun Medical, Inc. Vena Tech™ Vena Cava Filters, Feb. 2000.
Gianturco-Roehm, Bird's Nest® Vena Cava Filter.
Cordis Corporation, TrapEase™ Permanent Vena Cava Filter, "A Small, Easy and Verstaile System for Optimal Pulmonary Emboli Prevention", 2000 (4 pages).

*Primary Examiner*—Eduardo C. Robert
*Assistant Examiner*—David Comstock
(74) *Attorney, Agent, or Firm*—Neil D Gershon

(57) ABSTRACT

A vein filter movable between a collapsed position for delivery to the vessel and an expanded position for placement within the vessel. The first region of the filter has a mounting portion for mounting the vessel filter within the vessel and a first filter portion converging to form a first converging region at a first end portion, positioned radially and axially inwardly of an end of the mounting portion. The second region of the filter has a transverse dimension decreasing toward a second end portion opposite the first end portion to form a second filter portion at the second end portion on the opposing side of the filter from the first filter portion.

22 Claims, 13 Drawing Sheets

U.S. PATENT DOCUMENTS

| | | | |
|---|---|---|---|
| 4,781,177 A | 11/1988 | Lebigot | |
| 4,793,348 A | 12/1988 | Palmaz | |
| 4,817,600 A | 4/1989 | Herms et al. | |
| 4,832,055 A | 5/1989 | Palestrant | |
| 4,957,501 A | 9/1990 | Lahille et al. | |
| 4,990,156 A | 2/1991 | Lefebvre | |
| 4,994,069 A | 2/1991 | Ritchart et al. | |
| 5,059,205 A | 10/1991 | El-Nounou et al. | |
| 5,133,733 A | 7/1992 | Rasmussen et al. | |
| 5,152,777 A | 10/1992 | Goldberg et al. | |
| 5,234,458 A | 8/1993 | Metals | |
| 5,300,086 A | 4/1994 | Gory et al. | |
| 5,324,304 A | 6/1994 | Rasmussen | |
| 5,344,427 A | 9/1994 | Cottenceau et al. | |
| 5,350,398 A | 9/1994 | Pavcnik et al. | |
| 5,370,657 A | 12/1994 | Irie | |
| 5,375,612 A | 12/1994 | Cottenceau et al. | |
| 5,382,261 A | 1/1995 | Palmaz | |
| 5,383,887 A | 1/1995 | Nadal | |
| 5,405,377 A | 4/1995 | Cragg | |
| 5,531,788 A | 7/1996 | Dibie et al. | |
| 5,591,197 A | 1/1997 | Orth et al. | |
| 5,601,595 A | 2/1997 | Smith | |
| 5,626,605 A | 5/1997 | Irie et al. | |
| 5,634,942 A | 6/1997 | Chevillon et al. | |
| 5,681,347 A | 10/1997 | Catheart et al. | |
| 5,683,411 A | 11/1997 | Kavteladze et al. | |
| 5,690,671 A | 11/1997 | McGurk et al. | |
| 5,709,704 A | 1/1998 | Nott et al. | |
| 5,725,552 A | 3/1998 | Kotula et al. | |
| 5,733,294 A | 3/1998 | Forber et al. | |
| 5,733,329 A | 3/1998 | Wallace et al. | |
| 5,746,767 A | 5/1998 | Smith | |
| 5,755,779 A | 5/1998 | Horiguchi | |
| 5,755,790 A | 5/1998 | Chevillon et al. | |
| 5,776,162 A | 7/1998 | Kleshinski | |
| 5,795,322 A | 8/1998 | Boudewijn | |
| 5,810,874 A | 9/1998 | Lefebvre | |
| 5,836,968 A | 11/1998 | Simon et al. | |
| 5,853,420 A | 12/1998 | Chevillon et al. | |
| 5,893,869 A | 4/1999 | Barnhart et al. | |
| 5,895,398 A | 4/1999 | Wensel et al. | |
| 5,895,410 A | 4/1999 | Forber et al. | |
| 5,911,717 A | 6/1999 | Jacobsen et al. | |
| 5,968,071 A | 10/1999 | Chevillon et al. | |
| 5,976,172 A | 11/1999 | Homsma et al. | |
| 5,984,947 A | 11/1999 | Smith | |
| 6,007,558 A | 12/1999 | Ravenscroft et al. | |
| 6,013,093 A | 1/2000 | Nott et al. | |
| 6,042,598 A | 3/2000 | Tsugita et al. | |
| 6,059,825 A | 5/2000 | Hobbs et al. | |
| 6,063,113 A | 5/2000 | Kavteladze et al. | |
| 6,066,158 A | 5/2000 | Engelson et al. | |
| 6,080,178 A | 6/2000 | Meglin | |
| 6,093,199 A | 7/2000 | Brown et al. | |
| 6,096,052 A | 8/2000 | Callister et al. | |
| 6,099,549 A | 8/2000 | Bosma et al. | |
| 6,117,154 A | 9/2000 | Barbut et al. | |
| 6,123,715 A | 9/2000 | Amplatz | |
| 6,126,673 A | 10/2000 | Kim et al. | |
| 6,146,404 A | 11/2000 | Kim et al. | |
| 6,152,946 A | 11/2000 | Broome et al. | |
| 6,165,179 A | 12/2000 | Cathcart et al. | |
| 6,165,198 A | 12/2000 | McGurk et al. | |
| 6,168,579 B1 | 1/2001 | Tsugita | |
| 6,168,603 B1 | 1/2001 | Leslie et al. | |
| 6,171,327 B1 | 1/2001 | Daniel et al. | |
| 6,171,328 B1 | 1/2001 | Addis | |
| 6,179,851 B1 | 1/2001 | Barbut et al. | |
| 6,179,859 B1 | 1/2001 | Bates et al. | |
| 6,187,025 B1 | 2/2001 | Machek | |
| 6,193,739 B1 | 2/2001 | Chevillon et al. | |
| 6,214,025 B1 | 4/2001 | Thistle et al. | |
| 6,217,600 B1 | 4/2001 | DiMatteo | |
| 6,231,581 B1 | 5/2001 | Shank et al. | |
| 6,231,589 B1 | 5/2001 | Wessman et al. | |
| 6,235,044 B1 | 5/2001 | Root et al. | |
| 6,235,045 B1 | 5/2001 | Barbut et al. | |
| 6,241,746 B1 | 6/2001 | Bosma et al. | |
| 6,245,012 B1 | 6/2001 | Kleshinski | |
| 6,251,122 B1 | 6/2001 | Tsukernik | |
| 6,258,026 B1 | 7/2001 | Ravenscroft et al. | |
| 6,267,776 B1 | 7/2001 | O'Connell | |
| 6,273,901 B1 | 8/2001 | Whitcher et al. | |
| 6,280,451 B1 | 8/2001 | Bates et al. | |
| 6,280,457 B1 | 8/2001 | Wallace et al. | |
| 6,290,721 B1 | 9/2001 | Heath | |
| 6,331,184 B1 | 12/2001 | Abrams | |
| 6,342,062 B1 | 1/2002 | Suon et al. | |
| 6,342,063 B1 | 1/2002 | Devries et al. | |
| 6,344,041 B1 | 2/2002 | Kupiecki et al. | |
| 6,402,771 B1 | 6/2002 | Palmer et al. | |
| 6,436,120 B1 * | 8/2002 | Meglin | 606/200 |
| 6,436,121 B1 | 8/2002 | Blom | |
| 6,443,971 B1 | 9/2002 | Boylan et al. | |
| 6,443,972 B1 | 9/2002 | Bosma et al. | |
| 6,447,530 B1 | 9/2002 | Ostrovsky et al. | |
| 6,447,531 B1 | 9/2002 | Amplatz | |
| 6,458,139 B1 | 10/2002 | Palmer et al. | |
| 6,468,290 B1 | 10/2002 | Weldon et al. | |
| 6,482,222 B1 | 11/2002 | Bruckheimer et al. | |
| 6,506,205 B2 | 1/2003 | Goldberg et al. | |
| 6,517,559 B1 | 2/2003 | O'Connell | |
| 6,527,962 B1 | 3/2003 | Nadal | |
| 6,537,294 B1 | 3/2003 | Boyle et al. | |
| 6,540,767 B1 | 4/2003 | Walak et al. | |
| 6,551,342 B1 | 4/2003 | Shen et al. | |
| 6,562,058 B2 | 5/2003 | Sequin et al. | |
| 6,652,558 B2 | 11/2003 | Patel et al. | |
| 6,660,021 B1 | 12/2003 | Palmer et al. | |
| 6,695,878 B2 | 2/2004 | McGuckin et al. | |
| 6,783,538 B2 | 8/2004 | McGuckin et al. | |
| 6,793,665 B2 | 9/2004 | McGuckin et al. | |
| 6,890,340 B2 * | 5/2005 | Duane | 606/200 |
| 6,932,831 B2 | 8/2005 | Forber | |
| 6,958,074 B2 | 10/2005 | Russell | |
| 6,972,025 B2 | 12/2005 | WasDyke | |
| 6,989,021 B2 | 1/2006 | Bosma et al. | |
| 6,994,092 B2 * | 2/2006 | van der Burg et al. | 606/200 |
| 7,037,321 B2 | 5/2006 | Sachdeva et al. | |
| 7,097,651 B2 | 8/2006 | Harrison et al. | |
| 2002/0058911 A1 | 5/2002 | Gilson et al. | |
| 2002/0116024 A1 | 8/2002 | Goldberg et al. | |
| 2002/0193827 A1 | 12/2002 | McGuckin et al. | |
| 2003/0130680 A1 | 7/2003 | Russell | |
| 2003/0195555 A1 | 10/2003 | Khairkhahan et al. | |
| 2003/0208227 A1 | 11/2003 | Thomas | |
| 2003/0208253 A1 | 11/2003 | Beyer et al. | |
| 2005/0015111 A1 | 1/2005 | McGuckin et al. | |

FOREIGN PATENT DOCUMENTS

| | | |
|---|---|---|
| WO | WO 95 09567 | 4/1995 |
| WO | WO 99 25252 | 5/1999 |
| WO | WO 01 45590 | 6/2001 |
| WO | WO 01 62184 | 8/2001 |
| WO | WO 01 72239 | 10/2001 |
| WO | 0211812 | 2/2002 |
| WO | WO 03 063732 | 8/2003 |
| WO | WO 04 049973 | 6/2004 |

* cited by examiner

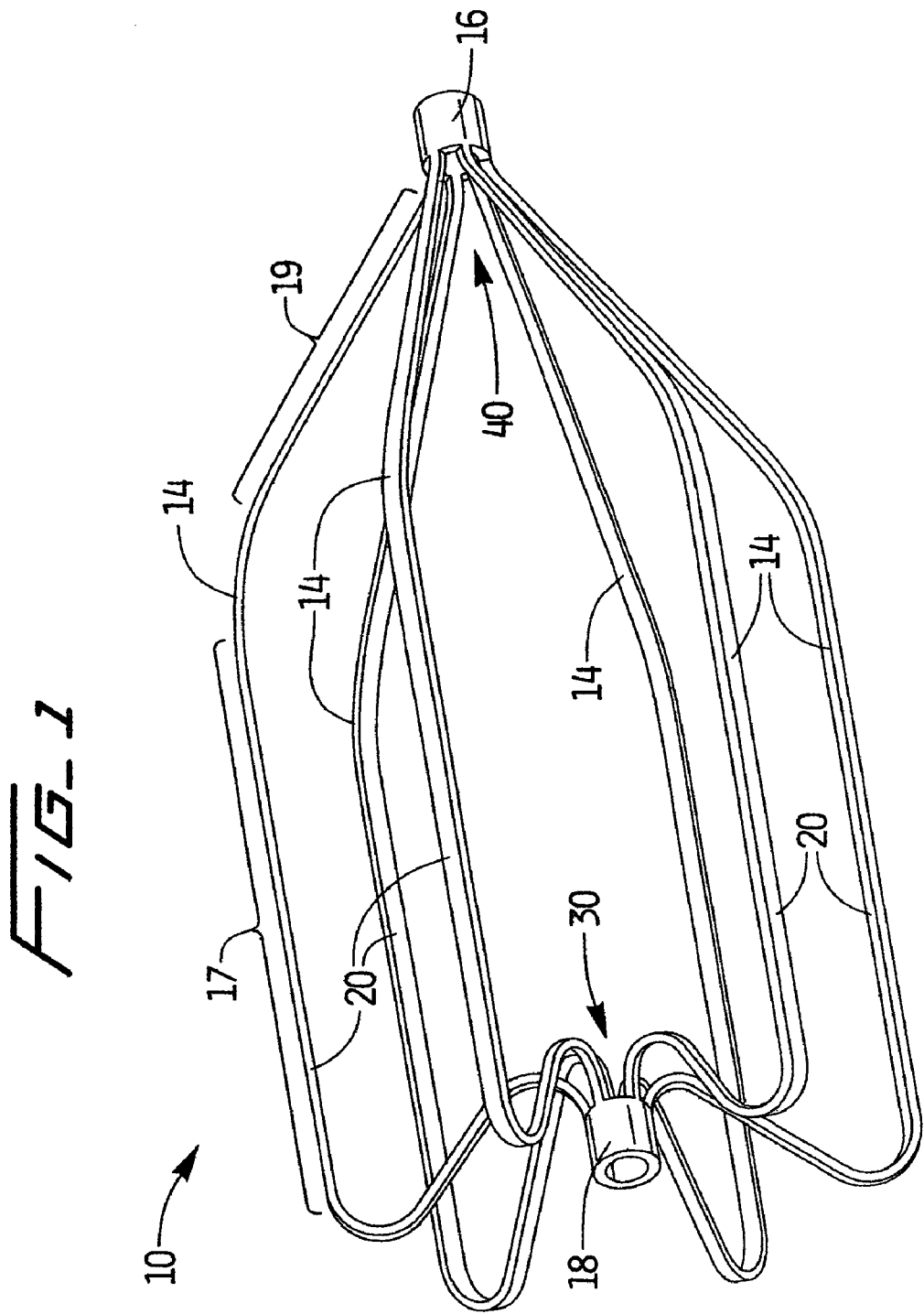

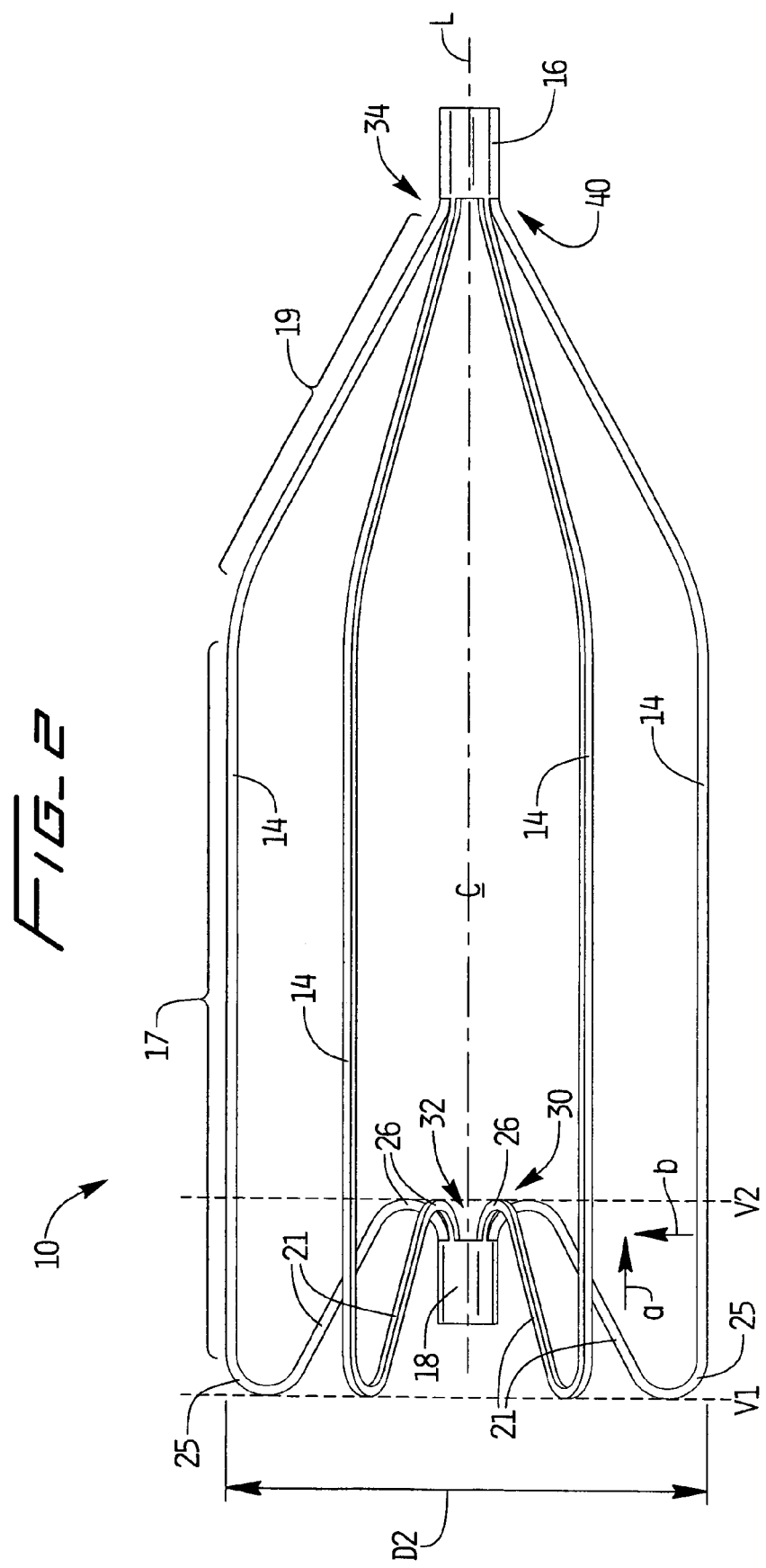

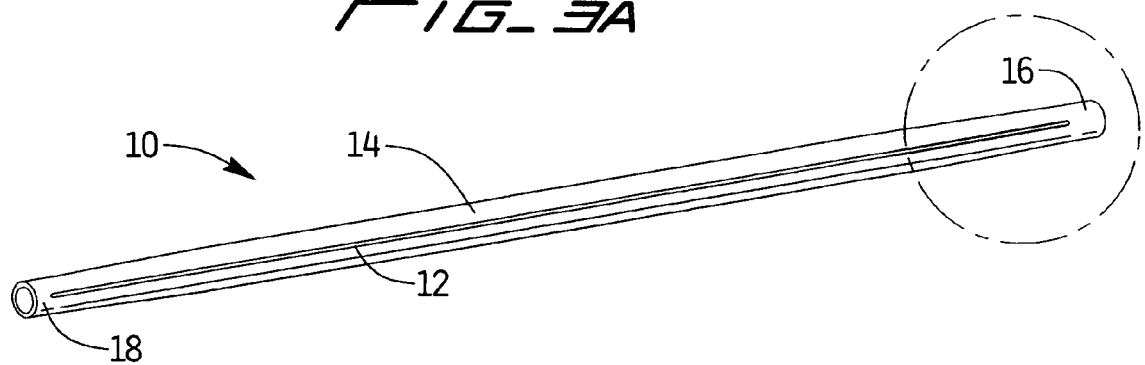
FIG_3A
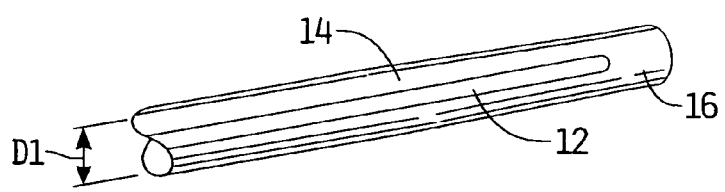
FIG_3B
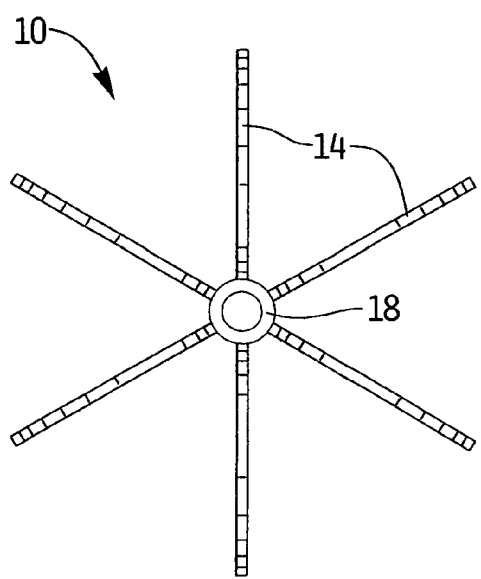
FIG_4

FIG_5A
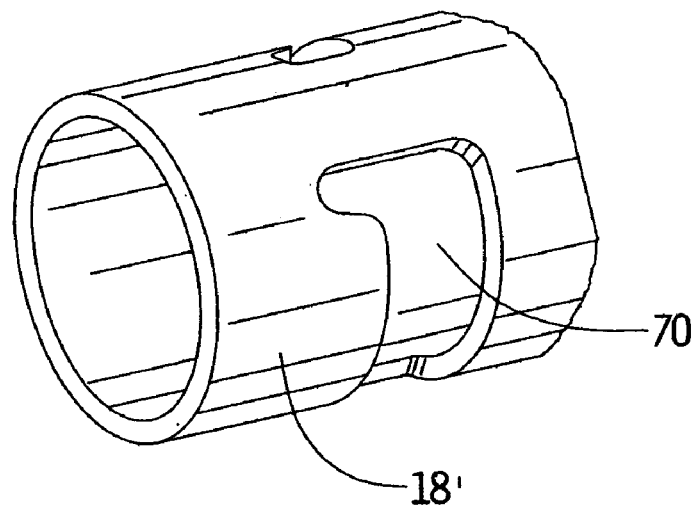
FIG_5B
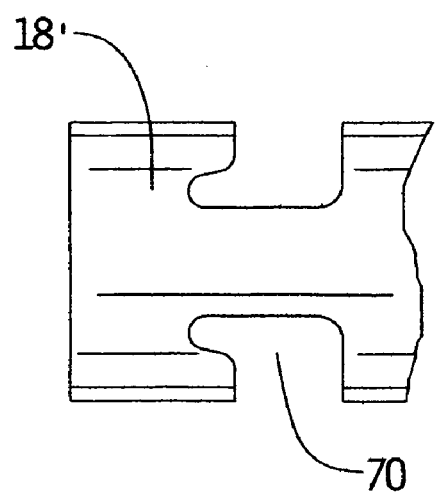

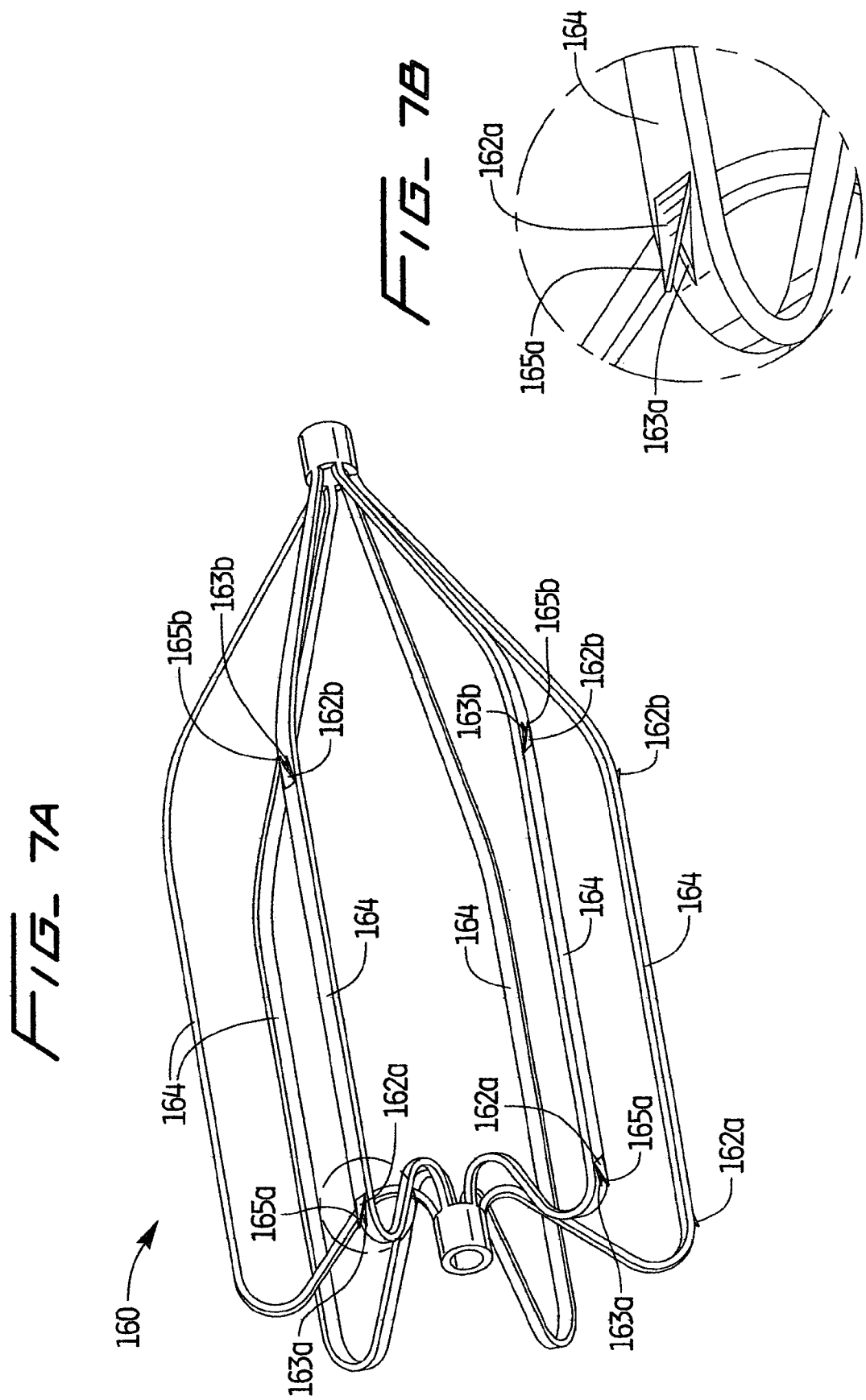

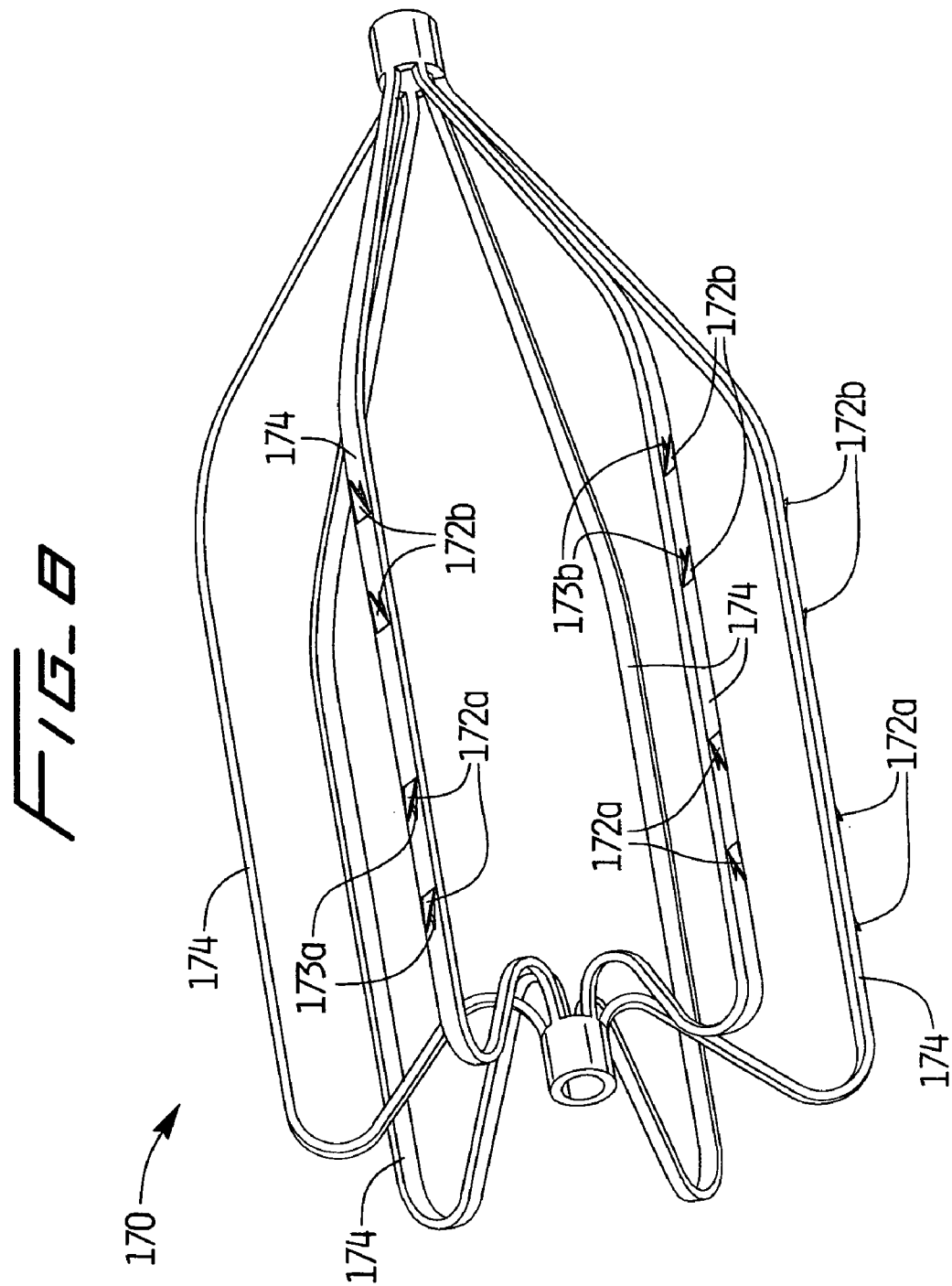

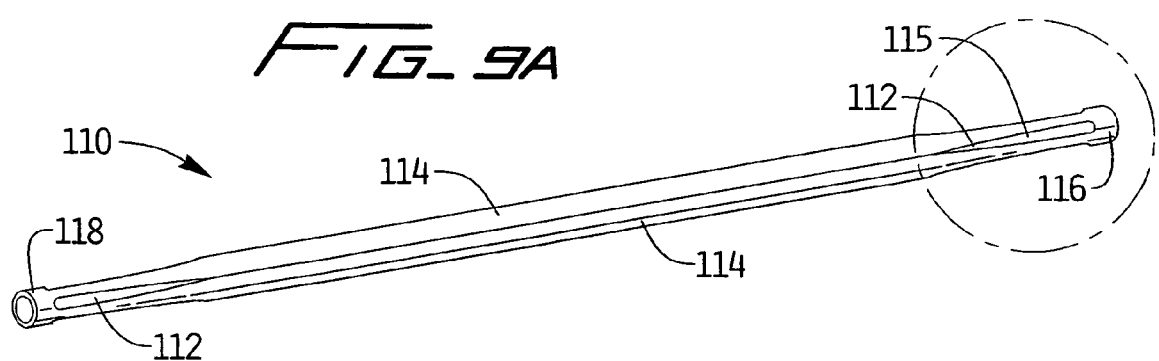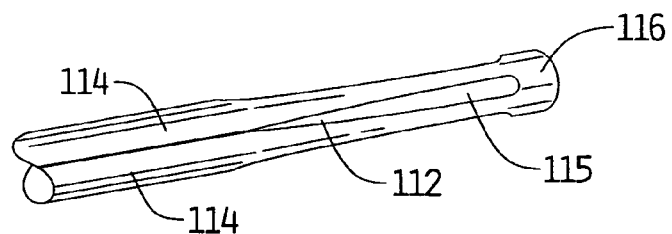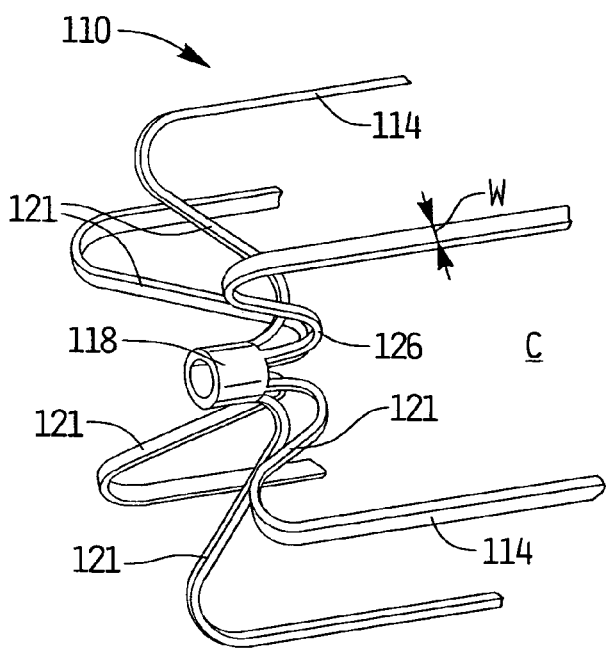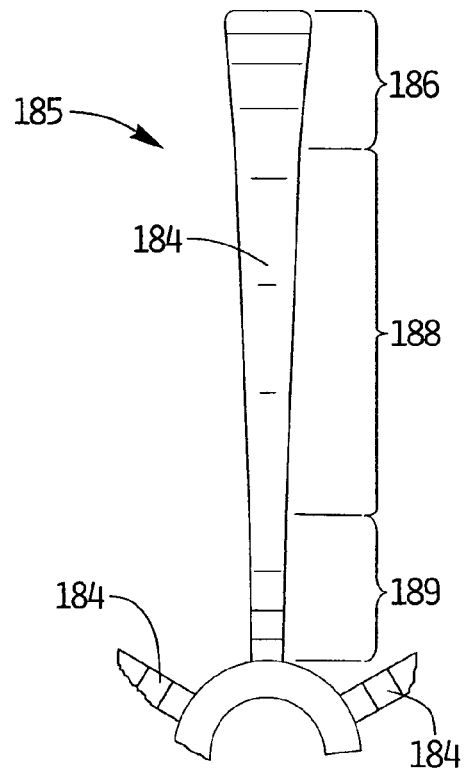

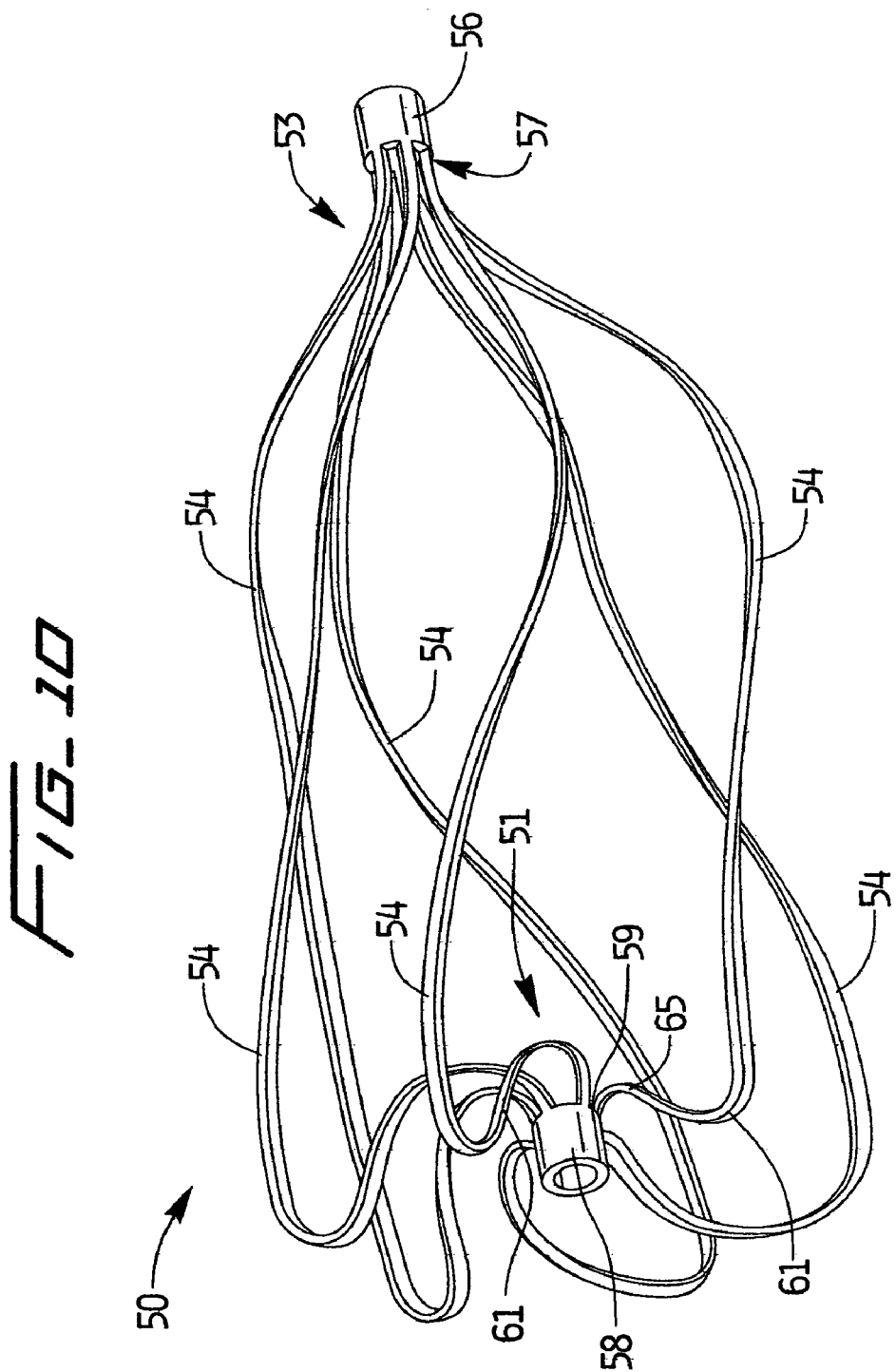

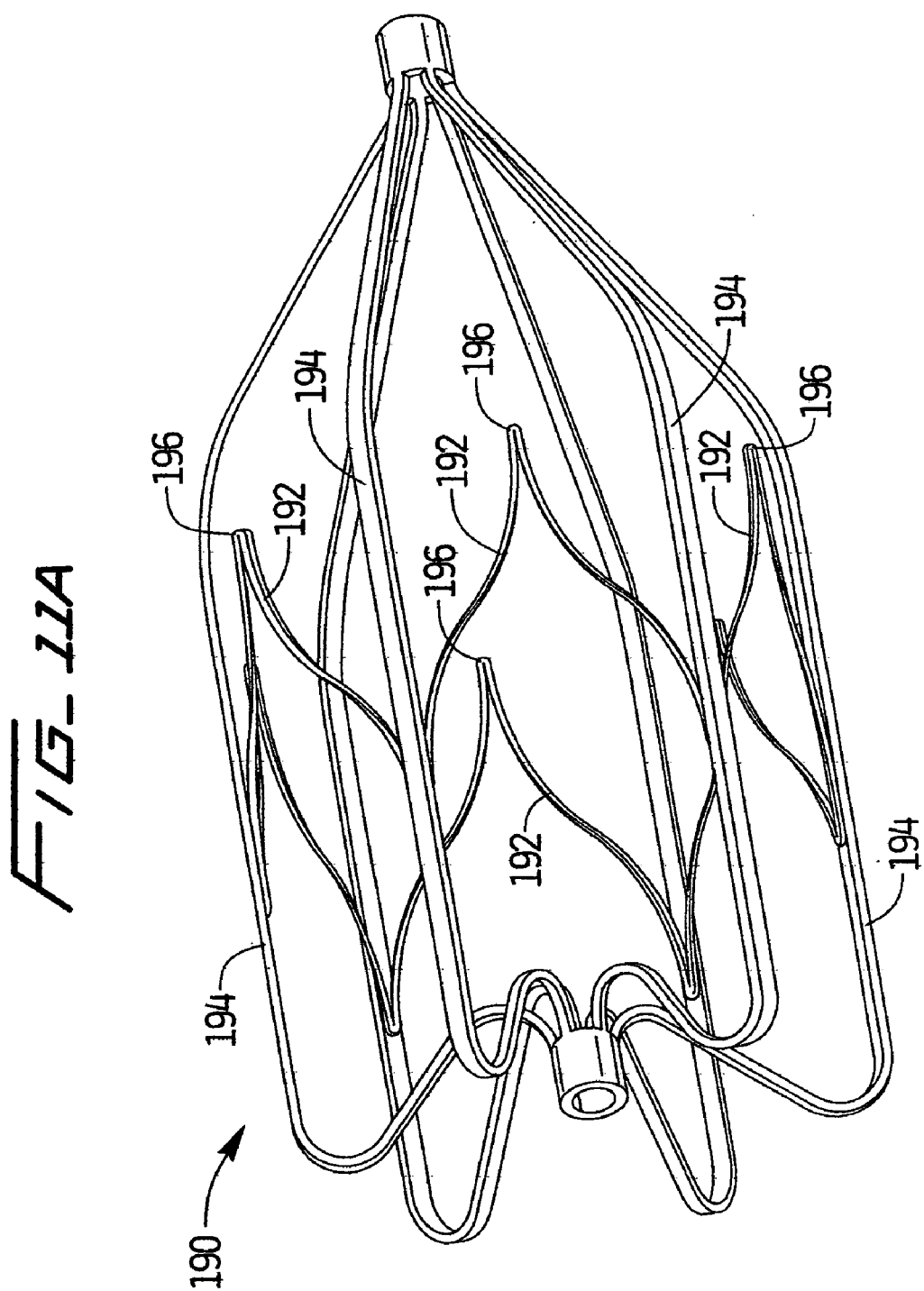

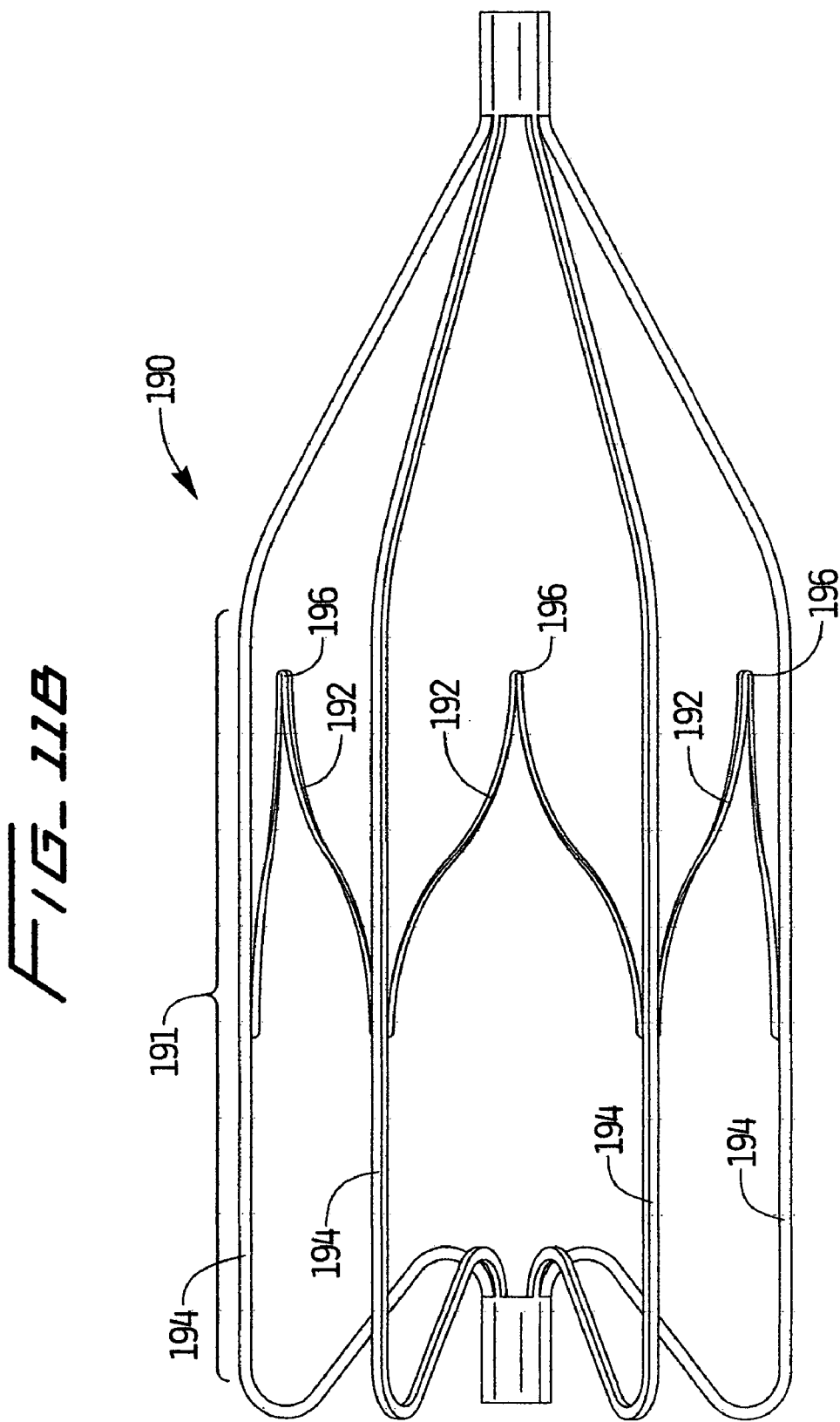

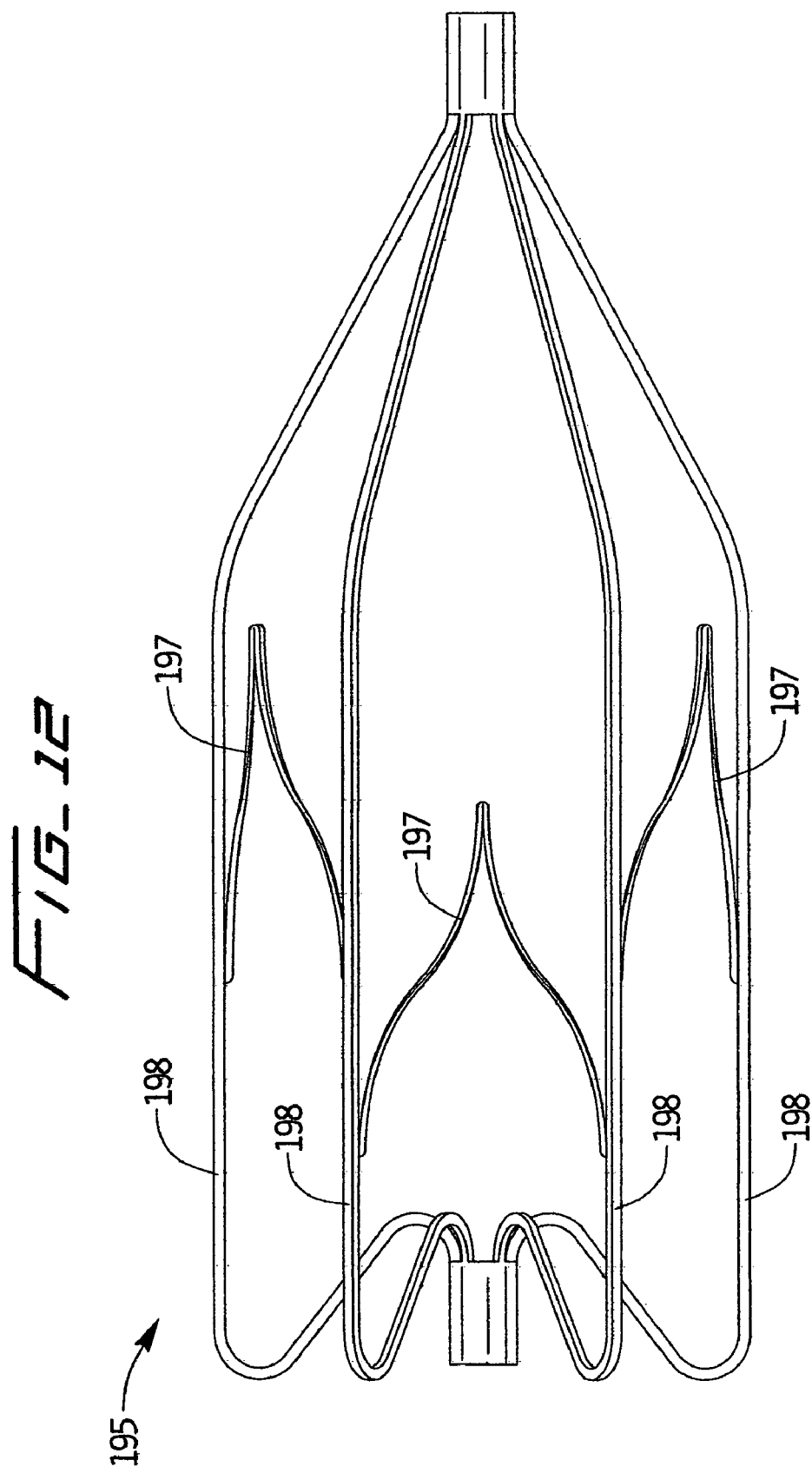
FIG_12

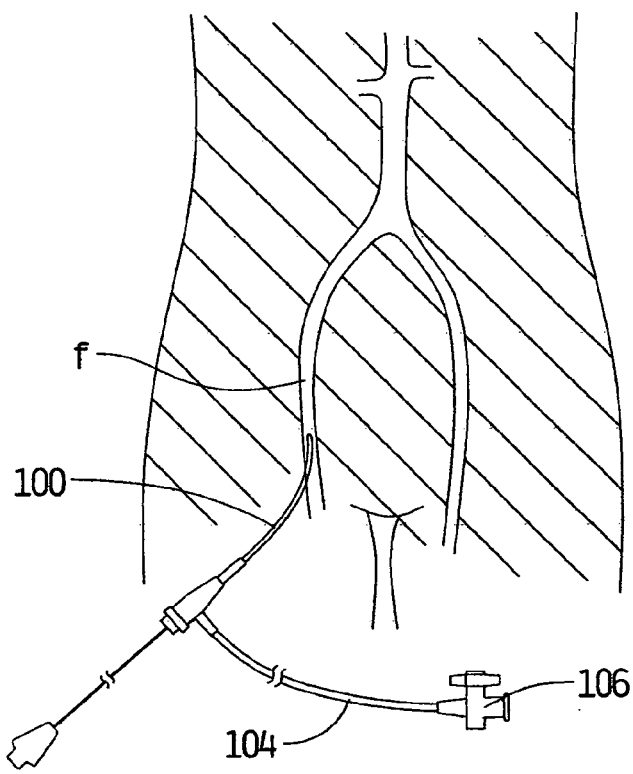
FIG_13
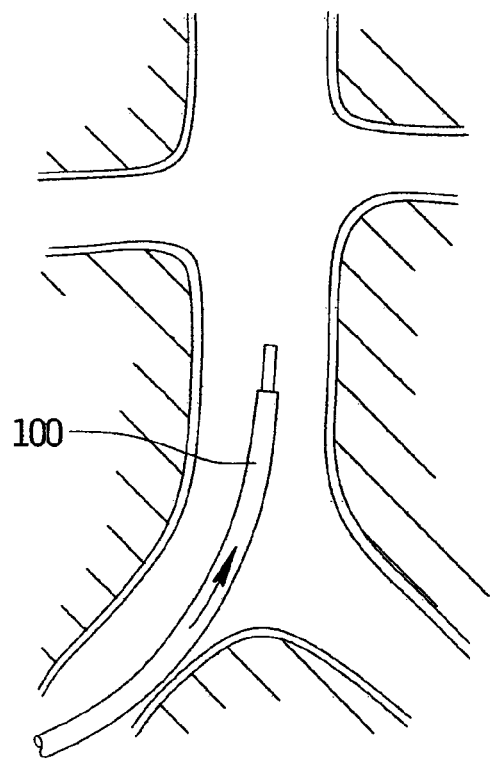
FIG_14
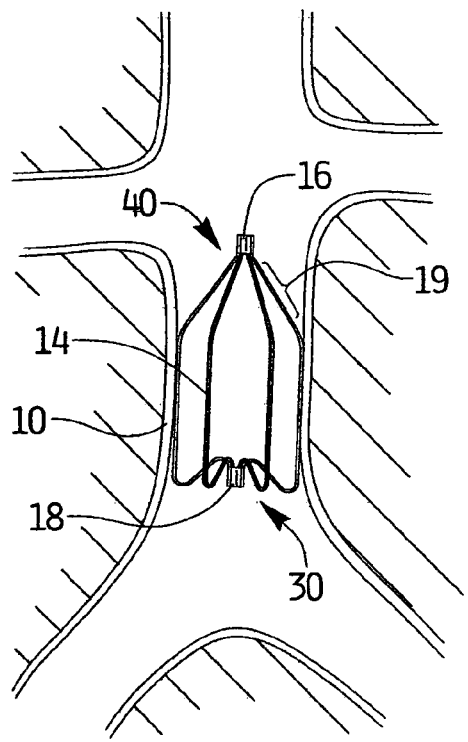
FIG_15

VEIN FILTER

This application claims priority from provisional patent application 60/466,807, filed Apr. 30, 2003 and is a continuation-in-part of application Ser. No. 10/638,846 filed Aug. 11, 2003 which is a continuation of Ser. No. 09/883,819, filed Jun. 18, 2001, now U.S. Pat. No. 6,623,506, the entire contents of each of these applications are incorporated herein by reference.

BACKGROUND

1. Technical Field

This application relates to a vascular filter and more particularly to a vein filter for capturing blood clots within the vessel.

2. Background of Related Art

Passage of blood clots to the lungs is known as pulmonary embolism. These clots typically originate in the veins of the lower limbs and can migrate through the vascular system to the lungs where they can obstruct blood flow and therefore interfere with oxygenation of the blood. Pulmonary embolisms can also cause shock and even death.

In some instances, blood thinning medication, e.g. anti-coagulants such as Heparin, or sodium warfarin can be given to the patient. These medications, however, have limited use since they may not be able to be administered to patients after surgery or stroke or given to patients with high risk of internal bleeding. Also, this medication approach is not always effective in preventing recurring blood clots.

Therefore, surgical methods to reduce the likelihood of such pulmonary embolisms by actually blocking the blood clot from reaching the lungs have been developed. One surgical method of treatment involved major surgery where the size of the vessel lumen was restricted by placement of ligatures or clips around the vein, e.g. the inferior vena cava which transports blood from the lower portion of the body to the heart and lungs. This prevented passage of dangerously large blood clots through the vein to the lungs. However, this approach is an invasive surgical procedure, requiring an abdominal incision and general anesthesia and frequently causing vessel thrombosis and lower extremity swelling. Also, there is a lengthy patient recovery time and additional hospital and surgeon expenses associated with this major surgery. In fact, oftentimes, the patients requiring the surgery are unhealthy and the major surgery and general anesthesia poses a risk in and of itself.

To avoid such invasive surgery, less invasive surgical techniques have been developed. These involve the placement of a mechanical barrier in the inferior vena cava. These barriers are in the form of filters and are typically inserted through either the femoral vein in the patient's leg or the right jugular vein in the patient's neck or arm under local anesthesia. The filters are then advanced intravascularly to the inferior vena cava where they are expanded to block migration of the blood clots from the lower portion of the body to the heart and lungs.

These prior filters take various forms. One type of filter is composed of coiled wires such as disclosed in U.S. Pat. Nos. 5,893,869 and 6,059,825. Another type of filter consists of legs with free ends having anchors for embedding in the vessel wall to hold the filter. These filters are disclosed, for example, in U.S. Pat. Nos. 4,688,553, 4,781,173, 4,832,055, and 5,059,205, 5,984,947 and 6,007,558.

Several factors have to be considered in designing vein filters. One factor is that the filter needs to be securely anchored within the vessel wall, while avoiding traumatic engagement and damage to the wall as well as damage to the neighboring abdominal aorta. Another factor is that the filter must be collapsible to a sufficiently small size to be easily maneuvered and atraumatically advanced intravascularly to the inferior vena cava or other target vessel. Thirdly, the filter should direct the blood clots to the center of the vessel to improve dissolution of the clot within the vessel by the blood flow.

It would be advantageous to provide a vein filter that satisfies the foregoing parameters. Namely, such vein filter would advantageously have sufficient anchoring force to retain the filter within the vessel while providing atraumatic contact with the vessel wall, would have a minimized insertion (collapsed) profile to facilitate delivery through the vascular system to the surgical site, and would enable migration of the captured blood clots to the center of the vessel. Moreover, it would also be advantageous to provide a filter that could simplify insertion through the femoral or the right jugular vein or arm into the inferior vena cava.

Additionally, the need for a vein filter in many patients is temporary. In these instances it would be advantageous to provide a vein filter that satisfies the foregoing factors and in addition could be readily removed from the patient. It would further be advantageous if the filter could be removed minimally invasively, e.g. intravascularly, and further advantageous if the filter could be removed from the inferior vena cava in either direction, e.g. through femoral or internal jugular vein access.

SUMMARY

The present invention overcomes the problems and deficiencies of the prior art. The present invention provides a vessel filter comprising a first region and a second region and movable between a collapsed position for delivery to the vessel and an expanded position for placement within the vessel. The first region has a mounting portion for mounting the vessel filter within the vessel and a first filter portion converging to form a first converging region at a first end portion. The first converging region is positioned radially and axially inwardly of an end of the mounting portion. The second region has a transverse dimension decreasing toward a second end portion opposite the first end portion to form a second filter portion at the second end portion on the opposing side of the filter from the first filter portion.

Preferably, the second filter portion converges to a second converging region. Preferably, portions of the filter extending from the first end of the mounting portion to the first converging region angle radially inwardly and toward a center of the filter to direct particles toward the center. The filter can be composed of shape memory material.

In one embodiment, the filter comprises elongated struts having roughened surfaces to engage the vessel wall to increase retention. In another embodiment, the filter comprises elongated struts having vessel engaging members with pointed ends to engage the vessel wall to increase retention.

In one embodiment, the filter includes a plurality of elongated struts extending from the first end portion to the second end portion wherein the opposing ends of at least one of the elongated struts are offset or out of phase.

The present invention also provides a vessel filter comprising a first region and a second region and movable between a collapsed position for delivery to the vessel and an expanded position for placement within the vessel. The first region has a mounting portion for mounting the vessel filter within the vessel and a first filter portion converging to form a first converging region at a first end portion. The second region has a transverse dimension decreasing toward a second end portion opposite the first end portion to form a second filter portion at the second end portion on the opposing side of the filter from the first filter portion. The second filter portion has a second converging region.

Preferably, the mounting portion has a substantially uniform transverse dimension, greater than the transverse dimension of the second region. Preferably, the vessel filter includes a plurality of elongated members having a first component substantially parallel to the longitudinal axis of the filter and a second component angled with respect to the longitudinal axis. Vessel engaging members can be provided to enhance retention of the filter.

The present invention also provides a vessel filter comprising a tubular member having a plurality of cutouts formed therein forming a series of elongated struts and movable between a first insertion configuration and a second deployed configuration. In the second configuration, the struts extend substantially longitudinally from a first end portion of the filter to an intermediate portion and from the intermediate portion to a second end portion of the filter at an angle to the longitudinal axis radially inwardly towards the longitudinal axis of the filter. A first filter portion has a first converging region and a second filter portion at the second end portion has a second converging region.

The elongated struts can include retention elements to engage the vessel wall to increase retention. In one embodiment, the end portions of at least one of the elongated struts are offset or out of phase.

In an alternate embodiment, one or more of the elongated struts has varying widths along its length.

In one embodiment, the vessel filter has a connecting rib extending between adjacent elongated struts.

A method of implanting a vessel filter in a patient's body is also provided comprising the steps of:

providing a vessel filter having a mounting section and first and second filtering sections each terminating in a converging end region, the first filtering section spaced axially inwardly from a tangent of the end of the mounting section and the second filtering section spaced axially outwardly from the mounting section away from a center of the filter;

providing a delivery member containing the vessel filter in a collapsed configuration having a first diameter;

inserting the vessel filter in the collapsed configuration adjacent a surgical site so that the first filtering section faces in the direction of blood flow and the second filtering section is downstream of the first filtering section; and deploying the vessel filter from the delivery member so the vessel filter moves to a placement configuration having a diameter larger than the first diameter and the first filtering section directs particles toward a center of the filter and the second filtering section directs particles bypassing the first filtering section to the center of the filter.

In one embodiment, the vessel filter is composed of shape memory material and movement of the vessel filter to the placement configuration moves the vessel filter towards a memorized configuration.

The method may also comprise the step of removing the implanted vessel filter from the patient's body.

BRIEF DESCRIPTION OF THE DRAWINGS

Preferred embodiment(s) of the present disclosure are described herein with reference to the drawings wherein:

FIG. 1 is a perspective view of a first embodiment of the vein filter of the present invention in the expanded configuration;

FIG. 2 is a side view of the vein filter of FIG. 1;

FIG. 3A is a perspective view of the vein filter of FIG. 1 in the collapsed configuration;

FIG. 3B is a close up view of one end of the vein filter of FIG. 3;

FIG. 4 is a front view of the vein filter of FIG. 1;

FIGS. 5A and 5B are close up and side views, respectively, of an alternate embodiment of an end of the filter having a cutout to receive a retrieval snare;

FIG. 7A is a perspective view showing an alternate embodiment of anchoring elements for anchoring the filter, the filter shown in the expanded configuration;

FIG. 7B is a close up view of an anchoring element of FIG. 7A;

FIG. 8 is a view similar to FIG. 7A except showing another alternate embodiment of anchoring elements;

FIG. 9A is a perspective view of the vein filter in a collapsed configuration in another alternate embodiment wherein the elongated struts have a varying width;

FIG. 9B is a close up view of an end portion of the filter of FIG. 9A;

FIG. 9C is a broken perspective view of one portion of the filter of FIG. 9A in the expanded configuration;

FIG. 9D is an enlarged partial front view of another alternate embodiment of the struts having a varying width;

FIGS. 10 is a perspective view of an alternate embodiment of the vein filter of the present invention with opposing strut end portions out of phase, the filter shown in the expanded configuration;

FIGS. 11A and 11B are perspective and side views of another alternate embodiment of the vein filter having stabilizing ribs extending between the struts;

FIG. 12 is a side view of an alternate embodiment of the vein filter of FIG. 1I having staggered stabilizing ribs;

FIGS. 13, 14 and 15 illustrate delivery and placement of the vessel filter of FIG. 1 in the inferior vena cava wherein FIG. 13 illustrates initial insertion of the delivery sheath through the femoral vein, FIG. 14 illustrates the delivery sheath being advanced toward the inferior vena cava just below (upstream) the juncture of the renal arteries; and FIG. 15 illustrates the delivery sheath fully withdrawn to place the filter in the expanded placement configuration in the inferior vena cava.

DETAILED DESCRIPTION OF PREFERRED EMBODIMENTS

Figure 6A:
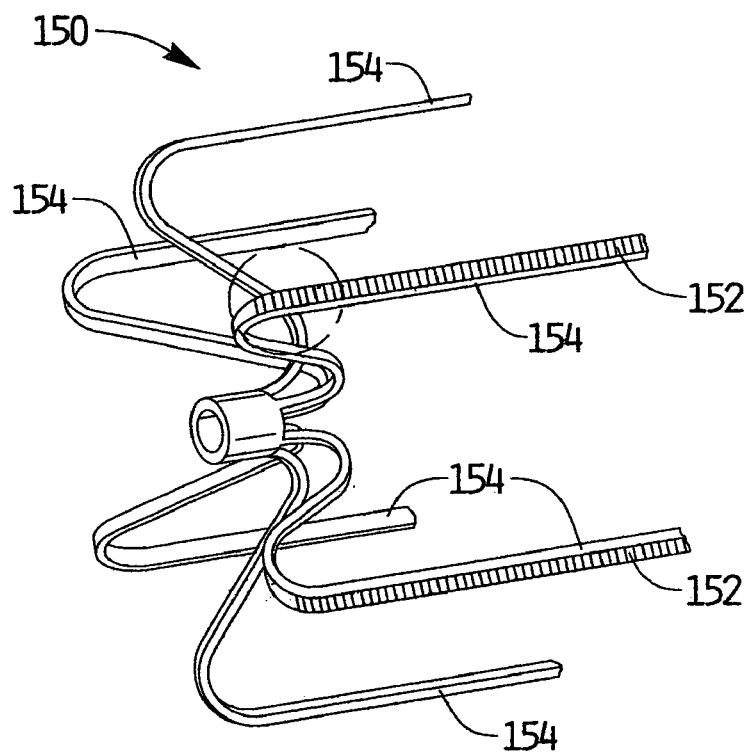
FIG. 6A is a broken perspective view of one portion of the filter in an expanded configuration showing a first embodiment of anchoring elements for anchoring the filter.

Turning now to the drawings, wherein like reference numerals identify similar or like components throughout the several views, the vein filter of the present invention is described for placement within the inferior vena cava to capture blood clots or other particles which could otherwise pass to the lungs. The filter is movable from a low profile collapsed configuration to facilitate insertion through the delivery sheath to a larger expanded placement configuration to enable atraumatic engagement with the vessel walls to secure (mount) the filter within the inferior vena cava. The filter has a mounting portion (section) and two filtering portions (sections) at opposing ends of the filter. As described in more detail below, the first filtering portion is spaced radially and axially inwardly from an end of the mounting portion and has a converging region. The second filtering portion is formed at the end of a tapered region and also has a converging region. In this manner, particles are directed toward a center of filter by the first filtering portion. If the particles bypass the first filtering portion, they are directed to the center by the second filtering portion. By directing the particles to the center, they will be exposed to greater blood flow which improves dissolution of the particles.

Turning now to details of the filter of the present invention and with initial reference to FIGS. 3A and 3B, the filter is designated generally by reference numeral 10 and is shown in a collapsed configuration for delivery. Filter 10 is preferably formed from a single tube. In a preferred embodiment, the filter 10 is composed of shape memory material, such as Nitinol, a nickel titanium alloy, however, other materials such as stainless steel are also contemplated. A plurality of cutouts 12 are formed in the filter 10, preferably by laser cutting although other techniques are contemplated. In the illustrated embodiment, six elongated cutouts are formed of substantially uniform width, creating six strips or struts 14 of substantially uniform width separated by the cutouts and terminating in tubular portions 16, 18 at the ends.

The collapsed configuration of filter 10 reduces the overall profile to facilitate delivery to the site. The diameter of filter 10 in the collapsed configuration is represented by reference D1 and preferably is about 2 mm and more preferably about 1.7 mm. Other dimensions are also contemplated. The diameter D2 of the filter in the expanded placement configuration (FIG. 2) is greater than the diameter D1 in the collapsed (delivery) configuration FIGS. 1 and 2 illustrate the expanded placement configuration of the filter 10. Filter 10 has a generally uniform region 17 and a tapered region 19. Region 17 generally forms the mounting section of the filter. In this configuration, the filter has expanded to a diameter D2. Diameter D2 preferably ranges from about 18 mm to about 32 mm, depending on the internal diameter of the vessel wall as will be explained in more detail below. Other dimensions are also contemplated. The elongated struts 14 are spaced apart as shown and extend substantially parallel to the longitudinal axis L of filter 10 in region 17. In the tapered region 19, beginning at an intermediate portion of the filter, the struts 14 angle inwardly toward the longitudinal axis, thereby forming an angle with the axis. In the illustrated embodiment, when expanded, the six struts 14 are shown spaced approximately 60 degrees apart. It is also contemplated that a fewer or greater number of struts could be provided and spacing other than 60 degrees be provided.

In the expanded placement configuration, each elongated strut 14 has an elongated outer surface 20 for engagement with the vessel wall to retain the filter 10 in position in the vessel. This region can be considered the substantially parallel component of the struts. The length of the elongated struts is preferably greater than the diameter of the filter 10 to provide additional longitudinal stability and decrease the likelihood of the filter rolling out of position. In a preferred embodiment the parallel component of each strut 14 is about 3.6 cm in length, although other dimensions are also contemplated. The angled component of the strut 14, defined in the tapered region 19, is preferably about 2.3 cm in length, although other dimensions are also contemplated.

Figure 6B:
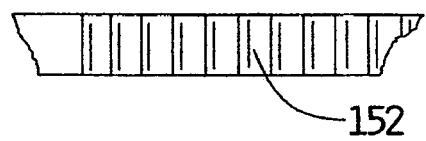
FIGS. 6B and 6C are close up and side views, respectively, of the anchoring elements of FIG. 6A.
Figure 6C:
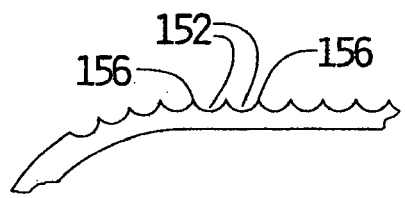

The outer surface 20 of struts 14 could be roughened to enhance engagement. Alternatively, a plurality of atraumatic tabs, barbs or other penetrating members can extend from the outer surface 20 of the strips 14 to engage the vessel wall to retain the filter. FIGS. 6, 7 and 8 show examples of such retention features. In FIGS. 6A–6C, filter 150 has a series of hemispherical cutouts 152 formed along the length of the struts 154 forming pointed edges 156 to engage the vessel wall. Although shown along the length of the strut 154, the cutouts 152 can alternatively be formed only along a portion of the length. The cutouts can also be formed on fewer than all the struts 154.

In the embodiment of FIG. 7A–7B, the filter 160 has anchoring elements 162a, 162b formed by cutouts 163 at the ends of the mounting section of the struts 164. Anchoring elements 162a have pointed ends 165a facing in a first direction towards the first end of the filter and anchoring elements 162b have pointed ends 165b facing in a second direction towards the second end of the filter. In the collapsed configuration the anchoring elements 162a, 162b and their pointed ends 165a, 165b are aligned with the struts 164, substantially parallel with the longitudinal axis of the filter to maintain a reduced profile. When the filter 160 moves to the expanded configuration, the pointed ends 165a, 165b face outwardly as shown in FIG. 7A. Anchoring elements 162a, 162b are preferably placed in the regions of the strut adjacent the curve or bend as shown, although other locations are also contemplated.

In the embodiment of FIG. 8, anchoring elements 172a, 172b of filter 170 are formed along the length of the struts 174 axially inwardly of the ends of the mounting portion. Anchoring elements 172a, 172b are similar to elements 162a, 162b in that they face in opposite directions as shown and are formed by cutouts 173a, 173b in the struts 174. They are also aligned with the struts 174 in the collapsed configuration in the same manner as anchoring elements 162a, 162b. In the view of FIGS. 7A and 8, anchoring elements 162a, 162b and 172a, 172b can be seen on only three of the struts, it being appreciated that they can be formed on all or any number of struts. Also, although six struts are shown, as with the other embodiments herein, a different number of struts is also contemplated.

Referring back to FIGS. 1 and 2, the filtering sections of filter 10 are on opposing ends of the filter as shown and are designated generally by reference numerals 30 and 40. First filtering section 30 extends from the mounting section 20, defined by region 17, and extends toward the center C of the filter 10 and converges at region 32 into tubular portion 18. Second filtering section 40 is positioned at the end of tapered region 19, at the opposite end of the filter, and converges at region 34 into tubular portion 16. Each elongated strut 14 extends substantially parallel to the longitudinal axis of the filter as described above up until tapered region 19. The end 25 of each elongated strut 14 adjacent the first end of the filter bend inwardly towards the center C of the filter 10 forming respective angled strut portion 21. These angled portions 21 thereby each extend both radially inwardly and axially inwardly toward the respective filtering section 30. The angled strut portions 21 transition to respective curved portions 26, curved in an outward direction to transition to the respective tubular portion 18 of the filtering section 30. For clarity, not all of these sections of each strut 14 are labeled in the drawing, it being understood that the non-labeled struts can have the same configurations.

It should be understood that the elongated struts 14 bend as they move from their collapsed position to their expanded placement configuration. Their designations of longitudinal, angled, curved, etc refer to the same integral strut and are divided into such regions for ease of understanding. Therefore, stated another away, the filter 10 can be viewed as having a filtering section 30 at one end and a filtering section 40 at a second opposing end with tubular portions 18, 16 at the two ends, respectively. As viewed, each of the struts 14 emerges from the tubular portion 16 in curved region 26 that initially extends inwardly toward the center C of the filter 10 and then curves outwardly away from the center C to transition to angled portion 21 which extends outwardly away from the center. The angled portions 21 bend inwardly at region 25 to transition to the longitudinal component of the strut 14. The struts 14 then extend longitudinally along the region 17 toward region 19, and then in region 19 extend radially inwardly toward tubular portion 16 to angle toward the central axis, creating a tapered region of the filter. Thus, filtering section 40 extends radially inwardly and axially outwardly from the longitudinal component of the strut.

The tubular portion 18 containing the converging region 32 of the filter 10 is spaced both axially inwardly and radially inwardly from the bend regions 25 which are at the end portion of the parallel components (or mounting section) of the strut 14. (Axially inwardly is represented by arrow "a" and radially inwardly is represented by arrow "b"). This can be appreciated by reference to FIG. 2, wherein imaginary vertical line V1 represents the end region of the mounting section, i.e. the strut 14, and vertical line V2 represents the end portion of the filtering section 30. V1 and V2 can also be viewed as tangent lines to the curved region of the mounting section and the curved region of the filter section, respectively.

The distances between V1 and V2 can be varied in design of the filter to alter the balance between the radial stretch of the filter and the ability to direct particles inwardly towards the center of the filter and vessel. That is, the greater the distance between V1 and V2, i.e. the greater the angle of the angled portions, the more the particles will be directed to the center of the filter and vessel. (Trapping the particles at the center rather than the edges of the filter is more desirable because there is less blood flow at the edges of the vessel and greater blood flow at the center to better dissolve the particles.) However, the greater the angle (formed by the angled portion of the strut and the longitudinal axis), the less radial stretch of the filter and the decreased ability to accommodate a wide variety of vessel sizes. The filters of the present invention are designed to optimize the balance of radial stretch to accommodate vessels of different sizes, e.g. 18 mm to 32 mm, with angled edges to direct particles toward the center of the vessel.

In the placement (expanded) configuration, the filter 10 moves towards its memorized position and the extent it returns to its fully memorized position will be dependent on the size of the vessel in which the filter 10 is inserted. (The larger the vessel, the closer the filter comes to returning to its fully memorized position).

To enable movement between an expanded and collapsed configuration, the filter tube of the embodiments described herein is preferably made of shape memory metal material, such as Nitinol, a nickel titanium alloy. The memorized configuration of the filter 10 is shown in FIG. 1. To facilitate passage of the filter 10 through the lumen of the delivery sheath 100 (shown in FIG. 13 in conjunction with the method of insertion) and into the vessel, cold saline is injected into the delivery sheath or catheter 100 and around the filter 10 in its collapsed position within the delivery sheath 100. This shape memory material characteristically exhibits rigidity in the austenitic state and more flexibility in the martensitic state. The cold saline maintains the temperature dependent filter 10 in a relatively softer condition as it is in the martensitic state within the sheath. This facilitates the exit of filter 10 from the sheath 100 as frictional contact between the filter 10 and the inner surface of the sheath would otherwise occur if the filter was maintained in a rigid, i.e. austenitic, condition.

Once ejected from the delivery sheath or catheter 100, the filter is no longer cooled and is exposed to the warmer body temperature, which causes the filter 10 to return towards its austenitic memorized configuration.

The filter 10 (and other filters described herein) can be inserted through the jugular vein in the neck of the patient or through the femoral vein in the leg of the patient or the arm. The filters can also be placed in the superior vena cava.

FIGS. 13–15 illustrate delivery and placement of the filter 10, by way of example, in the inferior vena cava. Delivery catheter 100 is inserted through the femoral vein "f" and advanced through the iliac arteries into the inferior vena cava. Delivery catheter would be withdrawn once the tip of the sheath is adjacent the structure so that withdrawal of the sheath would place the filter in the desired location of FIG. 15. Tubing 104 and valve assembly 106 enable saline injection. Delivery catheter 100 is withdrawn to enable filter 10 to be warmed by body temperature to transition to the expanded placement configuration. The other filters described herein could be inserted in the same manner. Note it is implanted in the orientation such that filter section 30 is upstream of filter section 40. This enables blood clots or other particles which are not captured by filter 30 to be directed to the center of the filter section 40 by the angled struts 14 at tapered region 19. Thus the direction of insertion, e.g. upstream or downstream direction, will determine how the filter is to be positioned in the delivery catheter.

In an alternate embodiment of FIGS. 9A–9C, the filter 110 has struts 114 which are wider, represented by reference letter w, at the elongated mounting region, (the parallel component), than at the angled portions 121 and curved regions 126. This is preferably achieved by removing material to create the thinner portions These thinner portions increase the flexibility of the filter for forming the angled portions upon deployment and the thicker portions increase the surface area contact with the vessel wall for mounting of the filter 110 within the vessel. FIGS. 9A and 9B illustrate the filter 110 in the collapsed configuration with cutouts 115 of non-uniform width cut into the tube to form the longitudinal struts 114. As shown, cutouts 112 are widest at the end regions 115, adjacent tubular portions 116 and 118 and thinner as they extend toward the center. This creates the widened region of longitudinal struts 114 when in the expanded placement configuration.

In an alternate embodiment, the filter can have elongated struts which are thinner, rather than wider as in the embodiment of FIG. 9A, at the elongated mounting region, than at the angled portions and curved regions. This would provide more stability at the curved regions. In the alternate embodiment of FIG. 9D, three different widths are provided. The zone 186 of filter 185 corresponding to the parallel component of the strut 184 has the greatest width, zone 188 corresponding to the angled portion of the strut 184 has a smaller width, and zone 189 corresponding to the curved region of the strut 14 has an even smaller width. The adjustment of the widths is designed to strike a balance between stability and flexibility of the various regions of the filter. Thus, other width variations are contemplated such as making zone 186 smaller in width than the zone 188 and/or zone 189, or providing a different number of width changes within each strut and/or in different struts.

In an alternate embodiment of FIG. 10, the end portions of each of the struts are offset or out of phase. This offset/radial shift results in particles bypassing the first filtering portion being captured by the second filtering portion since it is out of alignment. The offset can be achieved by twisting or rotating one of the ends of the filter. In one embodiment, the ends are about 30 degrees out of phase although other variations are contemplated. Filter 50 has struts 54, preferably six in number, formed so that the end 57 of each strut 54 at tubular portion 56 is out of axial alignment or phase with its opposing end 59 at tubular portion 58. This can be understood by appreciating an imaginary line (not shown) extending from one side of a strut 54 where it extends from tubular portion 56 to the opposing side of the same strut where it extends from tubular portion 58 would be at an angle to the longitudinal axis of the filter. Thus the filtering sections would be out of alignment. In contrast, in the non-offset embodiments, such imaginary lines would be substantially parallel with the longitudinal axis of the filter. As in the embodiments described above, the filtering portion 51 is positioned radially and axially inwardly of the end portion of the mounting section and filtering portion 53 is formed by the inwardly angled struts 54 of the tapered region, extending radially and axially outwardly. The struts 54 have angled or curved portions 61 extending radially and axially inwardly and bends at region 65 transitioning to respective tubular portions 58. For clarity, not all the struts 54 are so labeled.

In the alternate embodiment of FIG. 11A, connecting ribs 192 connect the struts 194 of filter 190. This increases the stability of the filter 190. As shown, the two ribs 192 extend from adjacent struts 194 and are joined at region 196. Thus, ribs 192 are preferably in the mounting section (region 191) and curve inwardly as shown. The ribs 192 can be arranged so they are axially aligned as in FIG. 11A or can be spaced axially as shown in the embodiment of FIG. 12 where ribs 197 between elongated struts 198 of filter 195 are axially displaced. The ribs can be placed between fewer than all the struts and the ribs can be utilized with any of the foregoing embodiments. Note that the ribs are shown attached to the struts, however, preferably the ribs would be integrally formed with the filter, formed by the laser cutting process mentioned above.

In another embodiment, the ribs could curve radially outward near their tips, thus contacting the vessel wall and acting as a retaining mechanism.

The foregoing filters can be inserted through the femoral vein or alternatively through the internal jugular vein. It can also be removed from either direction, e.g. from access through the inferior vena cava or through the internal jugular vein. Various methods can be used to remove the filter such as those described in commonly assigned co-pending application Ser. No. 09/911,097, filed Jul. 23, 2001, now published application 2002-0193827-A1, published Dec. 19, 2001, the entire contents of which is incorporated herein by reference, including for example, slotted hooks, graspers, etc. A recess or cutout can also be provided at the tubular end portions to receive a snare or other device for removal. Such recess is illustrated in the embodiment of FIGS. 5A and 5B and designated by reference numeral 70.

To facilitate removal of the filter from the vessel, cold saline can be injected onto the implanted filter to change the temperature of the filter to move it to a relatively softer condition to facilitate the filter being drawn in to the retrieval sheath. That is, injection of cold saline will cause the filter to approach its martensitic state, bringing the filter to a more flexible condition. The flexible condition facilitates the collapse and withdrawal of the filter into the retrieval sheath, by decreasing the frictional contact between the filter and the inner surface of the retrieval sheath.

While the above description contains many specifics, those specifics should not be construed as limitations on the scope of the disclosure, but merely as exemplifications of preferred embodiments thereof. For example, the filters can be inserted in other regions of the body. Also, any of the aforedescribed filters can have mounting sections of varying thickness. The foregoing filters can be made of materials other than shape memory material. Those skilled in the art will envision many other possible variations that are within the scope and spirit of the disclosure as defined by the claims appended hereto.

What is claimed is:

1. A vessel filter implantable in a vessel of a patient comprising a first region and a second region, the filter movable between a collapsed position for delivery to the vessel and an expanded position for placement within the vessel, the filter remaining in the expanded position in the vessel after a delivery device for the filter is withdrawn from the vessel, the first region of the filter having a mounting portion for mounting the vessel filter within the vessel and a first filter portion converging to form a first converging region at a first end portion, the mounting portion having a first end spaced from the second region, the first converging region being positioned radially and axially inwardly of the first end of the mounting portion such that the first end of the mounting portion is at a terminal end of the filter and the first filter portion is positioned closer to a center point of the filter than the first end of the mounting portion, the second region having a transverse dimension decreasing toward a second end portion opposite the first end portion to form a second filter portion at the second end portion on the opposing side of the filter from the first filter portion, the filter including a plurality of vessel engaging members to engage the vessel wall to secure the filter within the vessel when released from the delivery device and left within the vessel after withdrawal of the delivery device from the vessel.

2. The vessel filter of claim 1, wherein the second filter portion converges to a second converging region.

3. The vessel filter of claim 2, wherein the first and second converging regions converge to a tubular region.

4. The vessel filter of claim 1, wherein portions of the filter extending from the first end of the mounting portion to the first converging region angle radially inwardly and toward a center of the filter to direct particles toward the center.

5. The vessel filter of claim 1, wherein the filter comprises a plurality of elongated struts having roughened surfaces to engage the vessel wall to increase retention.

6. The vessel filter of claim 1, wherein the filter is composed of shape memory material.

7. The vessel filter of claim 1, wherein the filter includes a plurality of elongated struts extending from the first end portion to the second end portion, the opposing ends of at least one of the elongated struts being out of phase.

8. A vessel filter comprising a first region and a second region, the filter movable between a collapsed position for delivery to the vessel and an expanded position for placement within the vessel, the first region having a mounting portion for mounting the vessel filter within the vessel and a first filter portion converging to form a first converging region at a first end portion, the first converging region having a proximalmost end point, the mounting portion has a series of longitudinally extending members extending substantially parallel to a longitudinal axis of the filter to form an elongated outer surface for contact with the vessel wall when in the expanded position, the mounting portion having a proximalmost end point proximal of the proximalmost end point of the first converging region, the second region having a transverse dimension decreasing toward a second end portion opposite the first end portion to form a second filter portion at the second end portion on the opposing side of the filter from the first filter portion, the second filter portion having a second converging region, the second converging region having a distalmost end point, the distalmost end point being distal of the proximalmost end point of the first converging region and distal of the proximalmost end point of the mounting portion.

9. The vessel filter of claim 8, wherein the mounting portion has a substantially uniform transverse dimension, the dimension being greater than the transverse dimension of the second region.

10. The vessel filter of claim 9, further comprising vessel engaging members on the longitudinally extending members of the mounting portion to enhance retention of the filter.

11. The vessel filter of claim 8, wherein the longitudinally extending members transition into a second component angled with respect to the longitudinal axis.

12. A vessel filter comprising a tubular member having a plurality of cutouts formed therein forming a series of elongated struts and movable between a first insertion configuration and a second deployed configuration, in the second configuration the struts extend substantially longitudinally from a first end portion of the filter to an intermediate portion, the struts further extending at one end from the intermediate portion to a second end portion of the filter at an angle to the longitudinal axis radially inwardly towards the longitudinal axis of the filter and extending at another end radially inwardly towards the longitudinal axis and back towards the second end portion, a first proximal filter portion having a first converging region and a second distal filter portion having a second converging region and being positioned at the second end portion of the filter, the first converging region having a proximalmost end point and the second converging region having a distalmost end point, the struts further forming a mounting portion having a proximalmost end point proximal of the proximalmost end point of the first converging region.

13. The vessel filter of claim 12, wherein the elongated struts include retention elements to engage the vessel wall to increase retention.

14. The vessel filter of claim 13, wherein the retention elements have pointed members extending integrally from the elongated struts.

15. The vessel filter of claim 12, further comprising a connecting rib extending between adjacent elongated struts.

16. The vessel filter of claim 12, wherein end portions of at least one of the elongated struts are out of phase.

17. The vessel filter of claim 12, wherein the portion extending radially inwardly of at least one of the elongated struts has a width greater than a longitudinally extending portion of the strut.

18. The vessel filter of claim 12, wherein at least one of the elongated struts has varying widths along its length.

19. A method of implanting a vessel filter in a patient's body comprising the steps of:
providing a vessel filter having a mounting section and first and second filtering sections each terminating in a converging end region and a plurality of vessel engaging members, the first filtering section spaced axially inwardly from a tangent of the end of the mounting section and closer to a center of the filter so it is between a terminal end of the mounting section and the center of the filter, and the second filtering section spaced axially outwardly from the mounting section further from the center of the filter;
providing a delivery member containing the vessel filter in a collapsed configuration having a first diameter;
inserting the vessel filter in the collapsed configuration adjacent a surgical site so that the first filtering section faces in the direction of blood flow and the second filtering section is downstream of the first filtering section;
deploying the vessel filter from the delivery member so the vessel filter moves to a placement configuration secured within a vessel having a diameter larger than the first diameter and the first filtering section directs particles toward a center of the filter and the second filtering section directs particles bypassing the first filtering section to the center of the filter; and
withdrawing the delivery member from the vessel leaving the filter secured within the vessel in the large diameter placement configuration with the vessel engaging members engaging a wall of the vessel.

20. The method of claim 19, wherein the vessel filter is composed of shape memory material and movement of the vessel filter to the placement configuration moves the vessel filter towards a memorized configuration.

21. The method of claim 20, further comprising the step of removing the implanted vessel filter from the patient's body.

22. The method of claim 19, wherein the filter comprises a plurality of elongated struts, in the mounting region the struts have a curved region which curves in a distal direction and then curves back toward a proximalmost end.

* * * * *